United States Patent [19]

Allen

[11] Patent Number: 4,708,964

[45] Date of Patent: Nov. 24, 1987

[54] LIPOXYGENASE INHIBITORS

[75] Inventor: Larry M. Allen, Fort Collins, Colo.

[73] Assignee: Chemex Pharmaceuticals, Denver, Colo.

[21] Appl. No.: 578,414

[22] Filed: Feb. 9, 1984

[51] Int. Cl.$^4$ .................. A61K 31/34; A61K 31/065
[52] U.S. Cl. .................................... 514/533; 514/532; 514/570; 514/863; 514/826; 514/830; 514/859; 514/23; 514/464; 514/469; 514/64; 514/559; 514/718; 514/731
[58] Field of Search ............... 424/311, 312, 303, 319, 424/346, 145, 180; 514/513, 529, 863, 532, 533, 570, 863

[56] References Cited

U.S. PATENT DOCUMENTS

| | | | |
|---|---|---|---|
| 2,984,674 | 5/1961 | Rutschmann et al. | 260/340.5 |
| 3,054,802 | 9/1962 | Rutschmann et al. | 260/340.5 |
| 3,408,441 | 10/1968 | von Wartburg et al. | 424/180 |
| 3,502,770 | 3/1970 | Renz et al. | 424/195 |
| 3,524,844 | 8/1970 | Keller-Juslen et al. | 260/210 |
| 3,634,459 | 1/1972 | von Wartburg et al. | 260/340.5 |
| 3,896,238 | 7/1975 | Smith | 424/358 |
| 4,294,763 | 10/1981 | Kende et al. | 260/340.5 |
| 4,358,461 | 11/1982 | Maki et al. | 424/331 |
| 4,391,982 | 7/1983 | Kende et al. | 549/433 |
| 4,442,099 | 4/1984 | Nicolaou et al. | 424/248.57 |
| 4,451,475 | 5/1984 | Busse et al. | 424/270 |

OTHER PUBLICATIONS

Funk et al., A New Class of Lipoxygenase Inhibitor, Biochem. Biophys. Research Commun., 114(3), 937 (1983).
Bokech et al., Evidence for Inhibition of Leukotriene Au Synthesis by 5,8,11,14-Eicosatetraynoic Acid . . . , Chem. Abstracts 95:21862j (1981).
Walenga et al., . . . Inhibition of . . . Arachidonic Acid Metabolism . . . by Nordihydroguaiaretic Acid, Chem. Abstracts 93:201893n (1980).
Nicholas et al., Nordihydroguaiaretic Acid . . . as Inhibitors of . . . Lipoxygenase, Chem. Abstracts 87:147795t (1977).
Penneys et al., Inhibitor(s) of Prostoglandin Synthesis Psoriasis, Chem. Abstracts 89:73623c (1977).
F. Fiebrich, et al., "Silymarin, an Inhibitor of Lipoxygenase", Experientia 35(1979), p. 1548.
J. Baumann, et al., "Flavonoids and Related Compounds as Inhibitors of Arachidonic Acid Peroxidation", Prostaglandins, vol. 20, No. 4, pp. 627-637, Oct. 1980.
K. V. Honn, et al., "Nafazatrom (Bay g 6575) Inhibition of Tumor Cell Lipoxygenase Activity and Cellular Proliferation", FEBS Letters, vol. 139, No. 1, pp. 65-68, Mar., 1982.
R. V. Panganamala, et al., "Differential Inhibitory Effects of Vitamin E and other Antioxidants in Prostaglandin Synthetase, Platelet Aggregation and Lipoxidase, Prostaglandins, vol. 14, No. 2, pp. 261-264, Aug., 1977.
K. Yasumoto, et al., "Effect of Phenolic Antioxidants on Lipoxygenase Reaction", Agr. Biol. Chem., vol. 34, No. 8, pp. 1162-1168, 1970.
Y. Koshiara, et al., "Selective Inhibition of 5-Lipoxygenase by Natural Compounds Isolated from Chinese Plants, *Artemisia rubripes* Nakai", FEBS, vol. 158, No. 1, p. 41, Jul., 1983.
M. O. Funk, Jr., et al., "A New Class of Lipoxygenase Inhibitor. Polyunsaturated Fatty Acids Containing Sulfur", Bioch. and Bioph. Res. Comm., vol. 114, No. 3, pp. 937-943, 1983.
C. D. Perchonock, et al., "Dimethyleicosatrienoic Acids: Inhibitors of the 5-lipoxygenase Enzyme", Tetrahedron Letters, vol. 24, No. 24, pp. 2457-2460, 1983.
J. R. Pfister, et al., "Synthesis of Three Potential Inhibitors of Leukotriene Biosynthesis", J. Medicinal Chemistry, vol. 26, No. 8, pp. 1100-1103, 1983.
J. J. Voorhees, et al., "Leukotrienes and other Lipoxygenase Products in the Pathogenesis and Therapy of Psoriasis and Other Dermatoses", Arch. Dermatol., vol. 119, pp. 541-547, Jul. 1983.
H. W. Chan, "Soya-bean Lipoxygenase: an Iron-Containing Dioxygenase", Biochimica et Biophysica Acta, 327, pp. 32-35, 1973.
J. E. Greenwald, et al., "Role of Ferric Iron in Platelet Lipoxygenase Activity", Bioch. and Bioph. Res. Communications, vol. 96, No. 2, pp. 817-822, Sep. 30, 1980.
M. Hamberg, et al., "On the Specificity of the Oxygenation of Unsaturated Fatty Acids Catalyzed by Soybean Lipoxidase", J. Biol. Chem., vol. 242, No. 22, pp. 5329-5335, Nov., 1967.
N. Nelson, et al., "Prostaglandins and the Arachidonic Acid Cascade", Chem. & Eng. News, vol. 60, p. 30, Aug. 6, 1982.
B. Samuelsson, et al., "Introduction of a Nomenclature: Leukotrienes", Prostaglandins, vol. 17, No. 6, pp. 785-787, Jun. 1979.
B. Samuelsson, "Leukotrienes: Mediators of Immediate Hypersensitivity Reactions and Inflammation", Science, vol. 220, pp. 568-575, May 6, 1983.
R. H. Green, et al., "Leukotrienes", Tetrahedron, vol. 39, No. 10, pp. 1687-1721, 1983.

(List continued on next page.)

*Primary Examiner*—Ronald W. Griffin
*Attorney, Agent, or Firm*—Kenyon & Kenyon

[57] ABSTRACT

This invention provides methods of using a number of compounds for the inhibition of lipoxygenase in humans. Pathological conditions which may be treated by the compounds described herein include psoriasis, cellular proliferation, skin allergies, insect bites, allergic rhinitis, conjunctivitis, hay fever, bronchial asthma, allergic gastroenteritis, uterine contractions, hyperactivity of the colon and bronchospasms.

6 Claims, No Drawings

OTHER PUBLICATIONS

PCT Patent Application, K. C. Nicolau, "Luekotriene Analogues", filed in the U.S. Nov. 27, 1981, published in the PCT Gazette as No. WO 83/01897 on Jun. 9, 1983.

Satoshi Yamamoto, et al., "Turmor Promoter 12-O-Tetradecanoylphorbol-13-Acetate-Induced Insulin Secretion: Inhibition by Phospholipase $A_2$-And Lipoxygenase-Inhibitors", Biochemical and Biophysical Research Communications, vol. 105, No. 2, pp. 759-765, Mar. 30, 1982.

Teruo Nakadate, et al., "Inhibition of 12-O-Tetradecanoylphorbol-13-Acetate-Induced Epidermal Ornithine Decarboxylase Activity by Lipoxygenase Inhibitors: Possible Role of Product(s) of Lipoxygenase Pathway", Carcinogenesis, vol. 3, No. 12, pp. 1411-1414, 1982.

M. Volpi, et al., "Arachidonate Metabolite(s) Increase the Permeability of the Plasma Membrane of the Neutrophils to Calcium", Biochem. and Biophys. Res. Commun., 92:1231-1237, 1980.

H. L. Bumpers, et al., "The Effect of a Novel C-5 Inhibitor (K-76 COONa) on Tumor Cell Chemotaxis", J. Lab. and Clinic. Med., 102:421-427, 1983.

K. V. Honn, et al., "Prostacyclin, Thromboxanes, and Hemotogenous Metastasis", Advance. Prostagland. Thrombox. and Leukotriene Res., 12:313-318, 1983.

LIPOXYGENASE INHIBITORS

CROSS-REFERENCE TO RELATED APPLICATIONS

This application is related to commonly assigned U.S. application Ser. Nos. 578,413, abandoned, for "Tumor Reducing Compositions," Allen, and 578,412, abandoned, "Antioxidant Compounds and Methods of Synthesis," Allen, et al., being filed in the U.S. Patent Office concurrently herewith. The entire contents of those applications are incorporated herein by reference.

TECHNICAL FIELD

This invention relates to the use of certain organic compounds as inhibitors of the lipoxygenase pathway of the arachidonic acid.

BACKGROUND OF THE INVENTION

The assignee hereof has filed a number of applications referring to nordihydroguaiaretic acid (NDGA) and related compounds, and also mixtures of such compounds with metal salts, useful for the treatment of psoriasis, namely U.S. application Ser. No. 578, 501, abandoned, "Pharmacologically Active Mixtures of Organic Compositions and Metal Salts," Jordan, a continuation in part of Ser. No. 465,631, abandoned, being filed in the U.S. Patent Office concurrently herewith; U.S. application Ser. No. 578,549 "Methods of Treating Psoriasis and Inhibiting the Action of Lipoxygenase on Arachidonic Acid," Jordan, also being filed concurrently herewith; and U.S. Ser. No. 365,784, "Modification of Plant Extracts from Zygophyllaceae," Jordan.

The compounds herein are discussed in this assignee's applications filed concurrently herewith entitled "Tumor Reducing Compositions," Allen, and "Antioxidant Compounds and Methods of Synthesis," Allen, et al.

A number of lipoxygenase inhibitors are known. F. Fiebrich, et al., in "Silymarin, an Inhibitor of Lipoxygenase," *Experientia* 35 (1979) at 1548 report the silymarin marin constituents silybin, silydianin, and silychristin as lipoxygenase inhibitors.

J. Baumanor, et al., "Flavonoids and Related Compounds as Inhibitors of Arachidonic Acid Peroxidation," *Prostaglandins*, Vol. 20, No. 4, pp. 627-37, October, 1980, list a number of lipoxygenase and cyclooxygenase pathway inhibitors and compare their abilities to inhibit each pathway. The most effective lipoxygenase inhibitors listed are 2-aminoethyl-4-t-6-iodophenol (MK447), diphenylthiocarbazone, phenidone, BW 755C, 1,5-dihydroxynaphthalene, 2,3-dihydroxynaphthalene, 1,3-dihydroxynaphthalene, and mefenamic acid, of which the first two appear to have a high degree of specificity for lipoxygenase inhibition. This article also reports that silybin, rutin, tetrahydroxyethylquercetin, trihydroxyethylquercetin, monohydroxyethylquercetin, and monohydroxyethylrutin predominantly inhibit lipoxygenase, while luteolin, dihydroxyflavone, morin, and galangin inhibit both pathways. K. V. Honn, et al., in "Nafazatrom (Bay g 6575) Inhibition of Tumor Cell Lipoxygenase Activity and Cellular Proliferation," *FEBS Letters*, Vol. 139, No. 1, pp. 65-68, March, 1982, describe nafazatrom as a selective lipoxygenase inhibitor. R. V. Panganamala, et al, in "Differential Inhibitory Effects of Vitamin E and other Antioxidants in Prostaglandin Synthetase, Platelet Aggregation and Lipoxidase," *Prostaglandins*, Vol. 14, No. 2, pp. 261-64, August, 1977, describe dl-2-tocopherol, BHT and Trolox C as specific inhibitors of lipoxygenase and describe the following compounds as non-specific inhibitors of lipoxygenase: alpha-naphthol, propyl gallate and NDGA. K. Yasumoto, et al., in "Effect of Phenolic Antioxidants on Lipoxygenase Reaction," *Agr. Biol. Chem*, Vol. 34, No. 8, pp. 1162-68, 1970, list and rank (in order given) the following compounds as lipoxygenase inhibitors: NDGA, quercetin, propyl gallate, alpha-tocopherol, alpha-naphthol, homocatechol, pyrocatechol, BHA, BHT, hydroquinone, ploroglucinol, pyrogallol, resorcinol. Y. Kosihara, et al., in "Selective Inhibition of 5-Lipoxygenase by Natural Compounds Isolated from Chinese Plants, *Artemisia rubripes* Nakai," *FEBS*, Vol. 158, No. 1, p. 41, July, 1983, describe caffeic acid, eupatilin and 4'-demethyleupatilin as selective inhibitors of the 5-lipoxygenase pathway.

A number of compounds structurally similar to arachidonic acid and its derivatives have been disclosed as lipoxygenase inhibitors. M. O. Funk, Jr., et al., in "A New Class of Lipoxygenase Inhibitor. Polyunsaturated Fatty Acids Containing Sulfur," *Bioch. and Bioph. Res. Comm.*, Vol. 114, No. 3, pp. 937-43, 1983, describe 13-thia-9(Z),11(E)-octadecadienoic acid and 13-thia-9(E), 11(E)-octadecadienoic acid as soybean lipoxygenase inhibitors. C. D. Perchonock, et al., in "Dimethyleicosatrienoic Acids: Inhibitors of the 5-lipoxygenase Enzyme," *Tetrahedron Letters*, Vol. 24, No. 24, pp. 2457-60, 1983, describe 7,7'- and 10,10'-dimethyleicosa-5(Z), 8(Z), 11(Z)-trienoic acids as 5-lipoxygenase inhibitors. J. R. Pfister, et al, in "Synthesis of Three Potential Inhibitors of Leukotriene Biosynthesis," *J. Medicinal Chemistry*, Vol. 26, No. 8, p. 1100-03, 1983, describe 5,6-benzoarachidonic acid as a 5-lipoxygenase inhibitor. PCT patent application, K. C. Nicolau, "Leukotriene Analogues," filed in the U.S. Nov. 27, 1981, published in the PCT Gazette as No. WO 83/01897 on June 9, 1983, describes a number of leukotriene A4 derivative analogues having a cyclopropane instead of an epoxide ring, particularly 5,6-methanoleukotriene A4 analogues, as effective 5-lipoxygenase inhibitors. J. J. Voorhees, et al., "Leukotrienes and other Lipoxygenase Products in the Pathogenesis and Therapy of Psoriasis and Other Dermatoses," *Arch. Dermatol.*, Vol. 119, 541-47, July, 1983 list the following compounds as inhibiting the 5- and/or 12-lipoxygenase pathways: flavonoids, e.g. rutin or quercetin, ETYA (5,8,11,14 eicosatraynoic acid) and other acetylenic analogues of arachadonic acid, U-60, 257, a prostaglandin-type compound, NDGA, BW 755C, a pyrazoline derivative, timegadine, 5,6-methanoleukotriene A, and AA 861, a benzoquinone derivative.

Lipoxygenase has been shown to be an iron-containing enzyme, and H. W. Chan in "Soya-bean Lipoxygenase: an Iron-containing Dioxygenase," *Biochimica et Biophysica Acta*, 327, pp. 32-35, 1973, describes the chelators diphenylthiocarbazone, 1,10-phenanthroline, 2,2'-dipyridyl, 3-hydroxyquinoline, KCN and EDTA as inhibitors of soybean lipoxygenase. J. E. Greenwald, et al., in "Role of Ferric Iron in Platelet Lipoxygenase Activity," *Bioch. and Bioph. Res. Communications.*, Vol. 96, No. 2, pp. 817-822, Sept. 30, 1980, describe the ability of EDTA, EGTA, ferron and orthophenanthrolene to inhibit human platelet lipoxygenase as being in direct correlation with the avidity of these compounds for ferric ion.

M. Hamberg, et al., in "On the Specificity of the Oxygenation of Unsaturated Fatty Acids Catalyzed by Soybean Lipoxidase," *J. Biol. Chem.,* Vol. 242, No. 22, pp. 5329-5335, November, 1967, describe the stereospecificity of enzymatic attack on eicosatrienoic acids.

Arachidonic acid derivatives through the lipoxygenase pathway and their physiological effects have been discussed in a number of recent publications. Several key articles discussing the subject are: N. Nelson, et al., "Prostaglandins and the Arachidonic Acid Cascade," *Chem. & Eng. News,* Vol. 60, p. 30, Aug. 16, 1982; B. Samuelsson, et al., "Introduction of a Nomenclature: Leukotrienes," *Prostaglandins,* Vol. 17, No. 6, pp. 785-87, June, 1979; B. Samuelsson, "Leukotrienes: Mediators of Immediate Hypersensitivity Reactions and Inflammation," *Science,* Vol. 220, pp. 568-75, May 6, 1983; and R. H. Green, et al., "Leukotrienes," *Tetrahedron,* Vol. 39, No. 10, pp. 1687-1721, 1983. These chemicals have been reported as important in the promotion of skin tumors by TPA, in the promotion of chemotaxis of polymorphonuclear leukocytes in inflammation, in the promotion of the release of slow reacting substances of anaphylaxis, promotion of release of neutrophil lyosomal enzyme, promotion of release of glucose-induced insulin secretion, promotion of histamine release, stimulation of colonic secretions, stimulation of degranulation of neutrophils, and stimulation of thromboxane, prostaglandins and other cyclooxygenase pathway derivatives of arachidonic acid.

None of the foregoing prior art describes the ability of the compounds of this invention to inhibit lipoxygenase.

SUMMARY OF THE INVENTION

This invention provides methods of using a number of compounds for the inhibition of lipoxygenase in humans. Pathological conditions which may be treated by the compounds described herein include psoriasis, cell proliferation, skin allergies, insect bites, allergic rhinitis, conjunctivitis, hay fever, bronchial asthma, allergic gastroenteritis, uterine contractions, hyperactivity of the colon and bronchospasms.

DETAILED DESCRIPTION OF THE PREFERRED EMBODIMENTS

The compounds of this invention are selected from the group consisting of compounds of the following formulae:

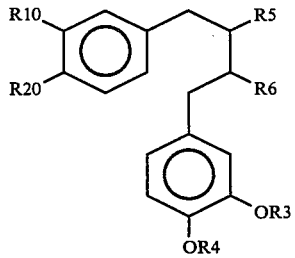

I.

where R1 is $-(CO)_n(CH_2)_m-COOR$ where n is 0 or 1, m is 1-4, and R is H, $CH_3$ or $C_2H_5$; sugar acid moieties, amino acid moieties, fatty acid moieties, and saccharide moities;
where R2-R4 are, independently, H or R1; and
where R5 and R6 are independently H and $CH_3$.

R1 is preferably ethylcarboxymethyl; O-ethyl-hemisuccinyl; alpha-D-glucopyranosyl; beta-D-glucopyranosyl, glycinyl; N-methylglycinyl; ethoxycarbonylmethoxy; hemisuccinyl aminoacetyl; N-methylacetyl; methyl carbamate, N-methyl, N-carbonyl; histidinyl; methylhistidinyl; spermidinylcarbonyl; and arachidonyl; and R5 and R6 are preferably $CH_3$.

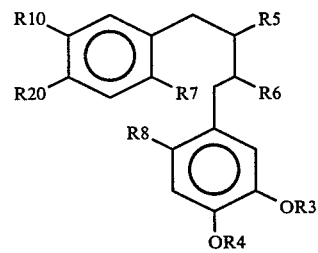

II.

where R1-R4 are independently H and $CH_3$, or R1 and R2 and/or R3 and R4 taken together are $CH_2$; R5 and R6 are independently H or methyl; and R7 and R8 are, independently H, $HSO_3$, and $NaSO_3$.

Preferably, R1-R4 are H, R5 and R6 are $CH_3$ and both R7 and R8 are $HSO_3$, or R7 is H and R8 is $NaSO_3$.

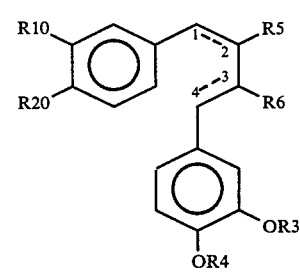

III.

where there are independently, double or single bonds at the 1 and 3 positions; and
where R1-R4 are independently H, $CH_3$, or R1 and R2 and/or R3 and R4 taken together are $CH_2$; and
where R5 and R6 are, independently, a 2-12 dienoic fatty acid moiety, a 1-12 mono- or dialkene, CHO, COOH, or taken together are succinic anhydride.

Preferably R1-R4 are all H or all methyl; and R5 and R6 taken together are succinic anhydride; or are both CHO, COOH, or nona-9-carboxy-1(E),4(E)-dienyl; or R5 is nona-9-carboxy-1(E),4(E)dienyl and R6 is deca-1(E),4(E)-dienyl.

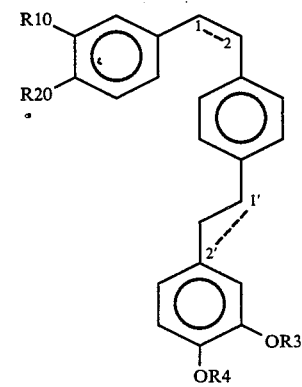

IV.

where there are, independently, double or single bonds at the 1 and 1' positions; and where R1–R4 are, independently, H, CH₃ or R1 and R2 and/or R3 and R4 taken together are CH₂.

Preferably R1–R4 are H or CH₃.

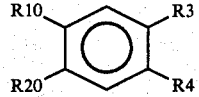   V.

where R1 and R2 are, independently, H and CH₃, or taken together, are CH₂;
where R3 is a dienoic 4–12 fatty acid moiety; and
where R4 is a dienoic 4–12 fatty acid moiety or a 4–12 mono or dialkene moiety.

Preferably R1 and R2 are H; and R3 is deca-1(E),-4(E)-dienyl or octa-2(Z)-enyl; and R4 is nona-9-carboxy,1(E)-4(E)-dienyl or deca-10-carboxy,2(Z),5(Z)dienyl.

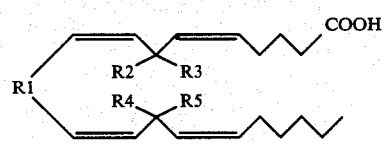   VI.

where R1 is CH₂, O, NH, CF₂ or CHF; and
where R2, R3, R4 and R5 are, independently, F and H.

Preferably R1 is CH₂ and R2 and R3 are F and R4 and R5 are H; or R1 is CH₂ and R2 and R3 are H and R4 and R5 are F; or R1 is CF₂ and R2, R3, R4 and R5 are H; or R1 is O and R2, R3, R4 and R5 are H; or R1 is NH and R2, R3, R4 and R5 are H. Where only one fluorine is present, it is preferred that this fluorine be such as to form an L-fluoro-compound.

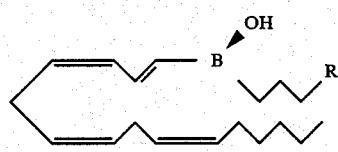   VII.

Where R is COOH, CH₃, or CHO.

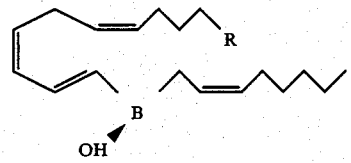   VIII.

Where R is COOH, CH₃ or CHO.

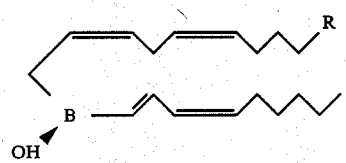   IX.

Where R is COOH, CH₃ or CHO

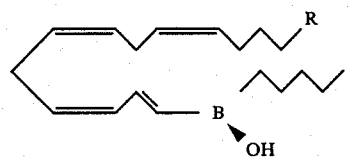   X.

Where R is COOH, CH₃ or CHO

Compounds illustrative of Formula I are: 1-(3,4-diethoxycarbonylmethoxyphenyl),4(3-hydroxy,4-ethoxycarbonylmethoxyphenyl),2,3-dimethylbutane; 1,4-bis(3-hydroxy,4-ethoxycarbonylmethoxyphenyl),2,3-dimethylbutane; nordihydroguaiaretic acid tetra-O-ethylhemisuccinate; nordihydroguaiaretic acid-alpha-D-glucopyranoside; nordihydroguaiaretic acid beta-D-glucopyranoside; nordihydro-guaiaretic acid-tetra-O-methylcarbamate; nordihydroguaiaretic acid-tetraglycinate; 1,4-bis(3-arachidonyl,4-hydroxyphenyl)-2,3-dimethylbutane; nordihydroguaiaretic acid tetra N-methylglycinate; nordihydroguaiaretic acid-tetra-spermidinylcarbonate; and nordihydroguaiaretic acid tetra-O-methylhistidinyl carbonate.

Compounds illustrative of Formula II are:
1,4-bis(3,4-dihydroxy,6-sulfonylphenyl),2,3-dimethylbutane; and 1-(3,4-dihydroxyphenyl),4-(3,4-dihydroxy,6-sodiumsulfonylphenyl),2,3-dimethylbutane.

Compounds illustrative of Formula III are:
alpha,beta bis(3,4-dihydroxybenzyl)succinic dialdehyde; alpha,beta bis(3,4-dihydroxybenzyl)succinic acid; alpha,beta bis(3,4-dihydroxybenzyl)succinic anhydride; 10,11-bis-(3,4-dihydroxybenzyl)-5(E),8(E),12(E),15(E)-eicosatetraenoic acid; 10,11-bis(3,4-dihydroxybenzyl)-5(E),8(E),12(E),15(E)eicosatetraen-1,20-dioic acid.

Compounds illustrative of Formula IV are:
1,4-bis-(3,4-dimethoxyphenethyl)benzene; and beta,beta-bis-(3,4-dihydroxyphenyl),1,4-divinylbenzene.

Compounds illustrative of Formula V are: 4-(deca-1(E),4(E)-dienyl-5-(nona-9-carboxy-1(E),4(E)dienyl)-catechol; and 4-(octa-2(Z)-enyl)-5-(deca-10-carboxy-2(Z),5(Z)-dienyl)catechol.

Compounds illustrative of Formula VI are 7,7-difluoro-5(E),8(E),11(E),14(E)eicosatetraenoic acid; 7(L)-fluoro-5(E),8(E),11(E),14(E)eicosatetraenoic acid; 10,10-difluoro-5(E),8(E),11(E),14(E)eicosatetraenoic acid; 10(L)-fluoro-5(E),8(E),11(E),14(E)eicosatetraenoic acid; 13,13-difluoro-5(E),8(E),11(E),1-4(E)eicosatetraenoic acid; 13(L)-fluoro-5(E),8(E),1-1(E),14(E)eicosatetraenoic acid; 10-oxanorarachidonic acid; 10-azanorarachidonic acid.

A compound illustrative of Formula VII is 5-hydroxyborono-6(Z),8(E),11(E),14(E)-eicosatetraenoic acid.

A compound illustrative of Formula VIII is 12-hydroxyborono-5(E),8(E),10(Z)14(E)eicosatetraenoic acid.

A compound illustrative of Formula IX is 11-hydroxyborono-5(E),8(E),12(Z),14(E)-eicosatetraenoic acid.

A compound illustrative of Formula X is 15-hydroxyborono-5(E),8(E),11(E),13(Z)-eicosatetraenoic acid.

Contemplated classes of compounds illustrating the above formulae are the compounds of Formulae I to IV; the compounds of Formula V; the compounds of Formulae VI to X; the compounds of Formulae VII to X; the compounds of Formula V in which R4 is a dienoic 4–12 fatty acid moiety and the compounds of Formulae VI to X; compounds having acid and glucosyl moieties as aids to solubility; compounds having chelating moieties, including catechols and acids, as aids to interaction of the compounds with multivalent metal salts to facilitate tissue penetration; and compounds including galactosides, furanosides, and those having ester and amino moieties, intended to act as prodrugs.

Pharmaceutically acceptable salts of the above include those having alkali, preferably sodium and other alkali metal cations, alkaline earth metal cations, and other metal cations including zinc, aluminum, trivalent chromium, yttrium, manganese, divalent cobalt, divalent nickel, magnesium, aluminum, copper, divalent iron, t rivalent cobalt, divalent cadmium, mercury, platinum, gallium, rubidium, molybdenum and vanadium. Preferred salts of the organic compounds are sodium and zinc salts.

The compounds of this invention can be administered by any means that effects inhibition of the lipoxygenase pathway in warm-blooded animals. For example, administration can be oral and/or parenteral, e.g. subcutaneous, intravenous, intraperitoneal, or most preferably topical. The dosage administration will be dependent upon the age, health, and weight of the recipient and the kind of concurrent treatment, if any, and frequency of treatment.

Daily dosage of active ingredient compounds can be determined by one skilled in the art, and generally will be from about 0.1 mg. to about 10 mg. per kg. of body weight when non-locally applied. When locally applied, at least about 100 mg. per square centimeter of diseased skin should be employed. The compounds can be employed in dosage forms such as tablets, capsules, powder packets or liquid solutions, or elixirs for oral administration; or for parenteral administration, sterile liquid solutions or suspensions. For topical use, the compounds may be prepared in aerosol sprays or preferably, creams and ointments such as vanishing creams and ointments having a polyethylene glycol base; and in other such carriers known to the art. It is preferred that ointments include agents to provide the necessary tackiness for adherence to the skin. In preparations for oral and parenteral use, the concentration of the compounds will be between about 0.1 and about 10 weight percent. For topical preparations, the concentration of the compounds will be between about 0.1 and about 30 weight percent, preferably between about 0.1 and about 5 weight percent. The active organic component may be present at high concentrations, but the dosage received by the patient will be limited to the amount which can be absorbed through the skin.

When the preparations described above are to be used topically, the curative effects thereof are enhanced by the addition of zinc chloride. Generally the molar ratio of zinc chloride to active compound should be between about 1 and about 3, and the zinc chloride should be present in the preparation at a weight concentration between about 0.5% and about 10%, and preferably between about 1% and about 5%.

The compounds described above have not been previously known to inhibit the lipoxygenase pathway of the arachidonic cascade; and as such they have a general utility in the treatment of a number of disease conditions. Such disease conditions include skin allergies, psoriasis, cellular proliferation, acne, insect bites, allergic rhinitis, conjunctivities, hay fever, bronchial asthma, allergic gastroenteritis, uterine contractions, hyperactivity of the colon and bronchospasms.

The following illustrations are provided as an aid to the skilled worker in practicing this invention:

ILLUSTRATION 1

Psoriatic plaques on the skin of a patient are softened by washing with a non-allergenic, neutral soap to remove all psoriatic flaking. While the lesions are still moist, they are treated initially with a single application of an ointment containing 10% active compound selected from the compounds listed below. The reaction is observed after 2 hours and again after 24 hours, and the strength of the reaction noted. If the reaction has stopped after 24 hours, or is weak, second and subsequent treatments are done with an ointment also containing 10% active compound; and also containing 1% or 5% zinc chloride depending on the strength of the reaction. The weaker the reaction, the higher the indicated concentration of zinc chloride. If the initial reaction appears strong after 24 hours, treatment with the initial ointment containing no zinc chloride is continued. Applications of ointment to the plaques are made approximately three times a week for two weeks or such lesser time as the lesions are healed. Active compounds are selected from the following list:

NDGA-tetra-spermidinylcarbonate; NDGA-tetra-O-methylhistidine; 1,4-bis-(3-arachidony1,4-hydroxyphenyl), 2,3-dimethylbutane; 1,4-bis-(3,4-dihydroxy,6-sulfonylphenyl), 2,3-dimethylbutane; 1-(3,4-dihydroxyphenyl),4-(3,4-dihydroxy,6-sulfonylphenyl),2,3-dimethylbutane; 1-(3,4-dihydroxyphenyl),4-(3,4-dihydroxy,6-sodiumsulfonylphenyl),2,3-dimethylbutane; 10,11-bis(3,4-dihydroxybenzyl)-5(E),8(E),12(E),15(E)-eicosatetraenoic acid; 10,11-bis(3,4-dihydroxybenzyl)-5(E),8(E),12(E),15(E)-eicosatetraen-1,20-dioic acid; 4-(deca-1(E),4(E)-dienyl),5-(nona-9-carboxy-1(E),4(E)-dienyl)catechol; 4-(octa-2(Z)-enyl)-5-(deca-10-carboxy-2(Z),5(Z) dienyl)catechol; 7,7-difluoro-5(E),8(E),1-1(E),14(E)eicosatetraenoic acid; 10,10-difluoro-5(E),-8(E),11(E),14(E)-eicosatetraenoic acid; 7(L)-fluoro-5(E),8(E),11(E),14(E)-eicosatetraenoic acid; 10(L)-fluoro-5(E),8(E),11(E),14(E)-eicosatetraenoic acid; 13,13-difluoro-5(E),8(E),11(E),14(E)-eicosatetraenoic acid; 13(L)-fluoro-5(E),8(E),11(E),14(E)-eicosatetraenoic acid; 10-oxanorarachidonic acid; 10-azanorarachidonic acid; 5-hydroxyborono-6(Z),8(E),11(E),14(E)-eico-satetraenoic acid; 12-hydroxyborono-5(E),8(E),10-(Z),14(E)-eicosatetraenoic acid; 11-hydroxyborono-5(E),8-(E),12(Z),14(E)-eicosatetraenoic acid; 15-hydroxyborono-5(E),8(E),11(E),13(Z)-eicosatetraenoic acid; alpha,beta-bis-(3,4-dihydroxybenzyl)succinic acid; alpha,beta-bis-(3,4-dihydroxybenzyl)succinic anhydride; alpha,beta-bis-(3,4-dihydroxybenzyl)succindialdehyde; NDGA tetracarbobenzyloxyglycinate; NDGA tetraglycinate; NDGA-tetra-N-methylglycinate; 1-(3,4-diethoxycarbonylmethoxyphenyl), 4-(3-hydroxy,4-ethoxycarbonylmethoxyphenyl), 2,3-dimethylbutane; 1,4-bis-(3-hydroxy,4-ethoxycarbonylmethoxyphenyl), 2,3-dimethylbutane; NDGA tetra-O-ethylhemisuccinate; nordihydroguaiaretic acid alpha-D-glucopyranoside; nordihydroguaiaretic acid beta-D-glucopyranoside; NDGA tetra-O-methylcarbamate; beta,beta-bis(3,4-dihydroxyphenyl)1,4-divinyl benzene; 1,4-bis(3,4-dimethoxyphenethyl) benzene.

ILLUSTRATION 2

Psoriatic plaques under the hair of a patient are softened by washing with a standard commercial coal tar shampoo to remove flaking. While the lesions are still moist, they are treated initially by two shampooings with a shampoo (e.g. Johnson & Johnson Baby Shampoo) containing 10% active compound selected from the compounds of Illustration 1. The reaction is observed after 2 hours and again after 24 hours, and the strength of the reaction noted. If the reaction has stopped after 24 hours, or is weak, second and subsequent treatments are done with a shampoo containing 10% active compound and also containing 1% or 5% zinc chloride, depending on the strength of the reaction. The weaker the reaction, the higher the indicated concentration of zinc chloride. If the initial reaction appears strong after 24 hours, treatment with the initial shampoo containing no zinc chloride is continued. Applications of shampoo to the plaques by two shampooings per application are made approximately three times a week for two weeks or such lesser time as the lesions are healed.

ILLUSTRATION 3

The ability of the compounds of Illustration 1 to inhibit lipoxygenase activity is verified by the method set forth in the following example. A molar concentration of each compound is used equal to that of the $ID_{50}$ for NDGA tested on a daily basis.

EXAMPLE

The following example provides the method of assay of lipoxygenase inhibition:
Spectrophotometer temperature was set at 25° C., chart speed at 24 nm/min., and wavelength at 234 nm. Into two silica cuvettes labeled "reference" and "sample" the following was pipetted:

| Reagents | Reference | Sample |
| --- | --- | --- |
| 1. Borate buffer | 2.325 ml | 2.322 ml |
| 2. Substrate | 150 microliter | 150 microliter |
| 3. DMSO/buffer (40% V/V) | 2.5 microliter or | 25 microliter or |
| 4. Inhibitor | 25 microliter | 25 microliter |
| 5. Enzyme | — | 3 microliter |

All reagents were prepared fresh daily.
Buffer used was 0.1M borate, pH 9. Substrate was soybean lipoxidase type V, $1.47 \times 10^6$ units/ml. The stock solution was diluted (10% V/V) with borate buffer, then three microliters of the diluted enzyme was used in the assay. The substrate was stored on ice.

The concentration of tested inhibitors used was an equimolar amount to that of the $ID_{50}$ for NDGA tested that day using a stock solution of 5 mg. NDGA dissolved in 0.2 ml. DMSO and brought to volume with 0.3 ml. borate buffer.

After adding reagents 1, 2 and 3 (for uninhibited control) or 4 (inhibitor) to each cuvette, both cuvettes were mixed vigorously for exactly 10 seconds. Both cuvettes were placed in the spectrophotometer and preincubated for one minute. Both cuvettes were removed and three microliters of the enzyme were added to the sample cuvette only, which was mixed by inverting ten times in 30 seconds. Both cuvettes were placed back in the spectrophotometer and the chart recorder was immediately started. The delta $A_{234}/2$ min. was calculated from the linear portion of the graph which typically began after four minutes of reaction.

For each inhibitor, three replicates were run plus an ininhibited control. A simultaneously run uninhibited control was necessary due to the decrease in enzyme activity with time.

The effects of known inhibitors, NDGA and alpha-naphthol were tested as positive controls. Results are set forth in the tables below.

| Effect of Alpha-Napthol on the Inhibition of Soybean Lipoxidase | | |
| --- | --- | --- |
| Concentration of alpha-Naphthol | $A_{234}$nm/min. | % Inhibition |
| $2.5 \times 10^{-5}$M | .230 | 12% |
| $6.2 \times 10^{-5}$M | .141 | 46% |
| $7.5 \times 10^{-5}$M | .074 | 72% |
| $8.8 \times 10^{-5}$M | .069 | 74% |
| $12.5 \times 10^{-5}$M | .021 | 92% |
| No Inhibitor | $.261 \pm .021$ (N = 5) | — |

| Effect of NDGA on the Inhibition of Soybean Lipoxidase | | |
| --- | --- | --- |
| Concentration of NDGA | $A_{234}$ nm/min. | % Inhibition |
| $1.3 \times 10^{-4}$M | 0.217 | 1% |
| $2.6 \times 10^{-4}$M | 0.186 | 14% |
| $3.2 \times 10^{-4}$M | 0.100 | 54% |
| $3.9 \times 10^{-4}$M | 0.035 | 84% |
| No Inhibitor | $0.218 \pm 0.002$ (N = 4) | — |

What is claimed is:
1. The method for treating psoriatic lesions in a host in need of such treatment comprising topically applying to said lesions an effective amount of a pharmaceutical preparation comprising a suitable pharmaceutical carrier and a compound selected from the compound of the formulae:

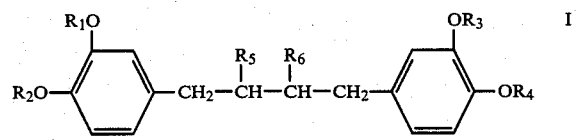

wherein
$R_1$ is $-OC)_n(CH_2)_m COOR$ and where n is 0 or 1, m is 1-4, and R is H, $-CH_3$ or $-C_2H_5$; or an acid moiety, including an amino acid moiety;
$R_2$, $R_3$ and $R_4$ are, independently, H or $R_1$; and
$R_5$ and $R_6$ are, independently, H or $-CH_3$;

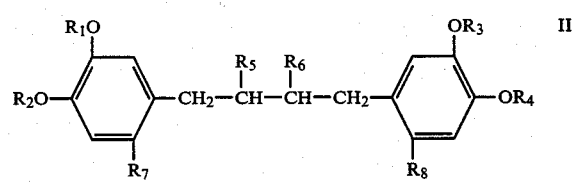

wherein
$R_1$, $R_2$, $R_3$ and $R_4$ are, independently, H or $-CH_3$; or $R_1$ and $R_2$ and/or $R_3$ and $R_4$ taken together are $-CH_2-$;
$R_5$ and $R_6$ are, independently, H or $-CH_3$; and
$R_7$ and $R_8$ are, independently, H, $-SO_3H$ or $-SO_3Na$; and

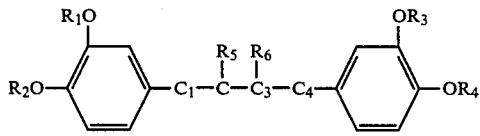

wherein there are, independently, double or single bonds in the 1-2 and 3-4 positions; and $R_1$, $R_2$, $R_3$ and $R_4$ are, independently, H, —$CH_3$, or $R_1$ and $R_2$ and/or $R_3$ and $R_4$ taken together are —$CH_2$—; and $R_5$ and $R_6$ are, independently, a 2–12 dienoic fatty acid moiety, a 1–12 mono- or dialkene, —CHO, —COOH or taken together are succinic anhydride.

2. The method of claim 1 in which said pharmaceutical preparation also contains zinc chloride in an amount of between about 0.5 and about 30 weight percent.

3. The method of claim 1 wherein said compound is selected from the group consisting of 1-(3,4-di-ethoxycarbonylmethoxyphenyl),4(3-hydroxy,4-ethoxycarbonylmethoxyphenyl),2,3-dimethylbutane; 1,4-bis(3-hydroxy,4-ethoxycarbonylmethoxyphenyl),2,3-dimethylbutane; and nordihydroguaiaretic acid tetra-O-ethylhemisuccinate.

4. The method of claim 3 wherein said compound is nordihydroguaiaretic acid tetra-O-ethylhemisuccinate.

5. The method of claim 3 wherein said compound is 1-(3,4-di-ethoxycarbonylmethoxyphenyl),4(3-hydroxy,4-ethoxycarbonylmethoxyphenyl),2,3-dimethylbutane.

6. The method of claim 3 wherein said compound is 1,4-bis(3-hydroxy,4-ethoxycarbonylmethoxyphenyl),2,3-dimethylbutane.

* * * * *